(12) United States Patent
Shinoki (10) Patent No.: US 10,555,665 B2
(45) Date of Patent: Feb. 11, 2020

(54) ENDOSCOPE REPROCESSOR AND ENDOSCOPE DEWATERING METHOD

(71) Applicant: OLYMPUS CORPORATION, Tokyo (JP)

(72) Inventor: Shohei Shinoki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/238,019

(22) Filed: Jan. 2, 2019

(65) Prior Publication Data

US 2019/0133428 A1    May 9, 2019

Related U.S. Application Data

(63) Continuation of application No. PCT/JP2017/008772, filed on Mar. 6, 2017.

(30) Foreign Application Priority Data

Sep. 21, 2016    (JP) ................. 2016-184489

(51) Int. Cl.
| | | |
|---|---|---|
| *A61L 2/08* | (2006.01) | |
| *A61L 2/00* | (2006.01) | |
| *A61B 1/00* | (2006.01) | |
| *A61B 1/12* | (2006.01) | |
| *G02B 23/24* | (2006.01) | |

(52) U.S. Cl.
CPC .......... *A61B 1/121* (2013.01); *A61B 1/00119* (2013.01); *A61B 1/00094* (2013.01); *G02B 23/2476* (2013.01)

(58) Field of Classification Search
CPC ....... A61B 1/121; A61B 1/00119; A61L 2/00; A61L 2/0088; A61L 2/16
USPC .......... 422/1, 26, 28, 33, 292, 300; 134/6, 8, 134/22.1, 22.12, 58 R; 600/133
See application file for complete search history.

(56) References Cited

U.S. PATENT DOCUMENTS 7,824,608 B2 * 11/2010 Kuroshima ............ A61B 1/123
                                                           134/22.11

FOREIGN PATENT DOCUMENTS

| JP | 2004-135946 A | 5/2004 |
| JP | 2009-207728 A | 9/2009 |
| JP | 2011-101773 A | 5/2011 |

OTHER PUBLICATIONS

International Search Report dated May 30, 2017 issued in PCT/JP2017/008772.

* cited by examiner

*Primary Examiner* — Monzer R Chorbaji
(74) *Attorney, Agent, or Firm* — Scully, Scott, Murphy & Presser, P.C.

(57) ABSTRACT

An endoscope reprocessor includes a first connector receptacle configured to connect a first connector connected to a cylinder in an endoscope, a first switching device configured to switch the first connector to one of a sealed state and an unsealed state, a first gas feeding device connected to an air introduction port to introduce gas, and a processor configured to perform control such that first driving for driving the first gas feeding device by bringing the first connector into the unsealed state is performed and second driving for driving the first gas feeding device by bringing the first connector into the sealed state is then performed.

7 Claims, 6 Drawing Sheets

ENDOSCOPE REPROCESSOR AND ENDOSCOPE DEWATERING METHOD

CROSS REFERENCE TO RELATED APPLICATION

This application is a continuation application of PCT/JP2017/008772 filed on Mar. 6, 2017 and claims benefit of Japanese Application No. 2016-184489 filed in Japan on Sep. 21, 2016, the entire contents of which are incorporated herein by this reference.

BACKGROUND OF THE INVENTION

1. Field of the Invention

The present invention relates to an endoscope reprocessor and an endoscope dewatering method.

2. Description of the Related Art

Conventionally, an endoscope reprocessor that feeds air into a conduit of an endoscope and discharges residual fluid such as a cleaning liquid or a disinfecting liquid or a rinsing liquid remaining in the conduit after a reprocessing process of the endoscope. Japanese Patent Application Laid-Open Publication No. 2009-207728, for example, discloses an endoscope reprocessor that feeds air into a scope connector in an endoscope and discharges residual fluid via an air/water feeding port in the endoscope reprocessor.

As another conventional example, Japanese Patent Application Laid-Open Publication No. 2011-101773 discloses an air/water feeding plug and a suction plug respectively mounted on an air/water cylinder and a suction cylinder in an endoscope.

When the air/water feeding plug and the suction plug are mounted, air introduced from a scope connector can reach a distal end of an insertion section, to remove water in a conduit from the scope connector to the distal end of the insertion section.

SUMMARY OF THE INVENTION

An endoscope reprocessor according to an aspect of the present invention includes a first connector receptacle configured to connect a first connector connected to a cylinder provided in an operation section in an endoscope and switchable to one of a sealed state where gas does not leak out of the endoscope from the cylinder and an unsealed state where gas leaks out of the endoscope from the cylinder, a first switching device configured to switch the first connector to one of the sealed state and the unsealed state, a first gas feeding device configured to introduce gas by being connected to a gas introduction port provided in a scope connector in the endoscope and feed gas to a distal end of the endoscope via the cylinder, and a processor configured to control the first switching device and the first gas feeding device such that first driving for driving the first gas feeding device by bringing the first connector into the unsealed state is performed and second driving for driving the first gas feeding device by bringing the first connector into the sealed state is then performed.

An endoscope dewatering method according to an aspect of the present invention includes bringing a connector for air/water cylinder inserted into an air/water cylinder in an endoscope into an unsealed state where gas leaks out of the endoscope from the air/water cylinder to introduce gas from an air supply connector and a water supply connector in the endoscope, and then bringing the connector for air/water cylinder into a sealed state where gas does not leak out of the endoscope from the air/water cylinder to introduce gas from the air supply connector and the water supply connector in the endoscope.

An endoscope dewatering method according to an aspect of the present invention includes bringing a connector for suction cylinder inserted into a suction cylinder in an endoscope into an unsealed state where gas leaks out of the endoscope from the suction cylinder to introduce gas from a suction connector in the endoscope, and then bringing the connector for suction cylinder into a sealed state where gas does not leak out of the endoscope from the suction cylinder to introduce gas from a suction connector in the endoscope.

DETAILED DESCRIPTION OF THE PREFERRED EMBODIMENT(S)

Figure 1:
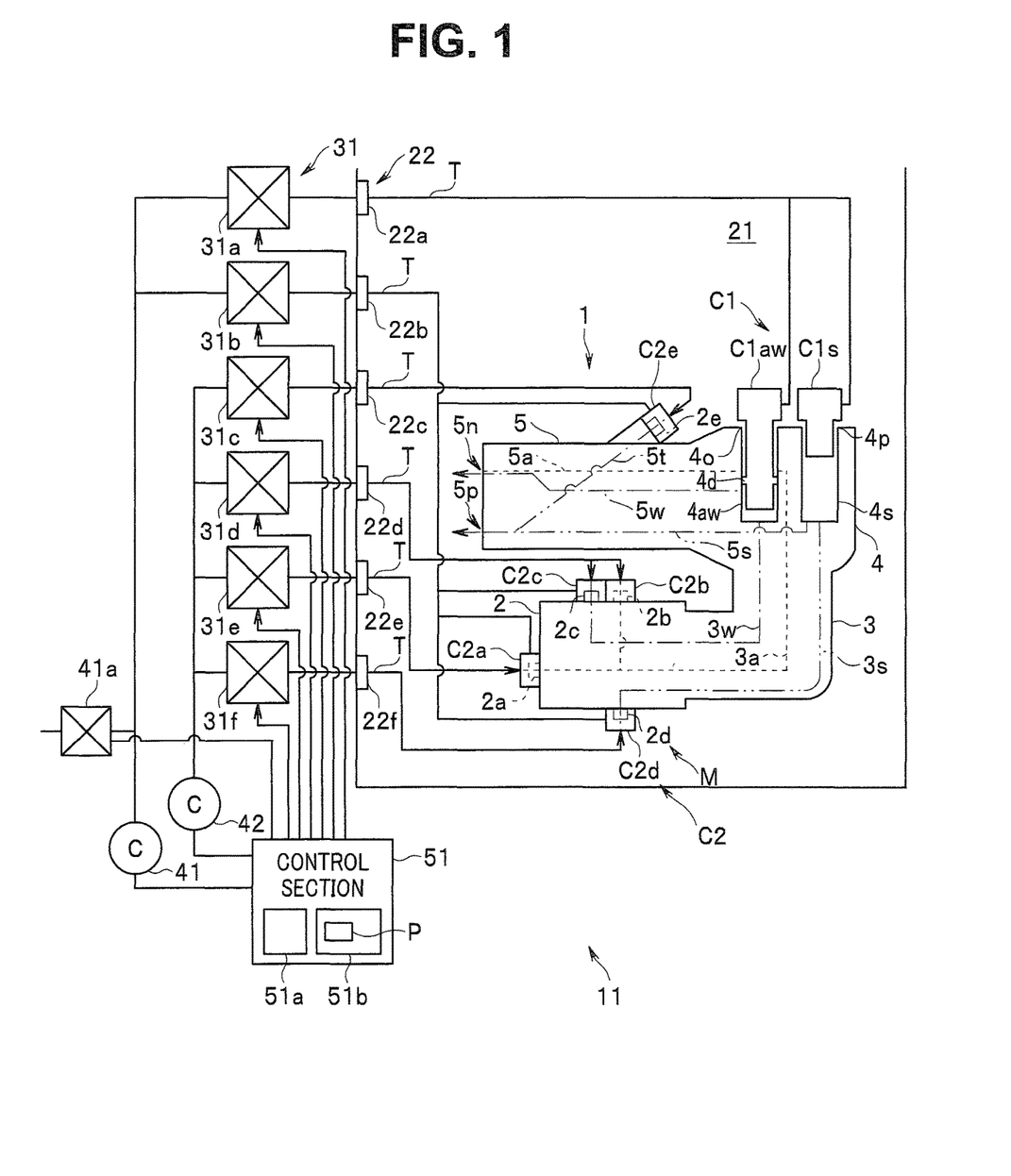
FIG. 1 is a schematic configuration diagram illustrating a configuration of an endoscope and an endoscope reprocessor according to an embodiment of the present invention.

An embodiment of the present invention will be described below with reference to the drawings.
(Configuration)
FIG. 1 is a schematic configuration diagram illustrating a configuration of an endoscope 1 and an endoscope reprocessor 11 according to the embodiment of the present invention.
(Configuration of Endoscope 1)
First, a configuration of the endoscope 1 will be described.

The endoscope 1 includes a scope connector 2, a universal cord 3 provided to extend from the scope connector 2, an operation section 4 connected to the universal cord 3, and an insertion section 5 provided to extend from the operation section 4.

The scope connector 2 includes air supply connectors 2a and 2b, a water supply connector 2c, and a suction connector 2d.

Each of the air supply connector 2a and 2b communicates with an air/water cylinder 4aw provided in the operation section 4 via an air channel 3a. The air/water cylinder 4aw communicates with an air/water nozzle 5n provided in a distal end portion of the insertion section 5 via an air channel 5a (a broken line in FIG. 1).

The water supply connector 2c also communicates with the air/water cylinder 4aw via a water channel 3w. The air/water cylinder 4aw also communicates with a water channel 5w. The water channel 5w is connected to the air channel 5a within the insertion section 5 and communicates with the air/water feeding nozzle 5n (a dot and dash line in FIG. 1).

The suction connector 2d communicates with the suction cylinder 4s provided in the operation section 4 via a suction channel 3s. The suction cylinder 4s communicates with a distal end opening 5p provided in the distal end portion of the insertion section 5 via a suction channel 5s (a two-dot and dash line in FIG. 1).

An instrument channel port 2e is provided in the vicinity of the operation section 4. The instrument channel port 2e is connected to the suction tube 5s via an instrument channel 5t, and communicates with the distal end opening 5p.

The operation section 4 includes the air/water cylinder 4aw and the suction cylinder 4s as cylinders into which an air/water valve and a suction valve (not illustrated) are to be respectively inserted.

The air/water cylinder 4aw includes a cylinder opening 4o. The air channels 3a and 5a and the water channels 3w and 5w are connected to the air/water cylinder 4aw, to enable the air channels 3a and 5a to communicate with each other and enable the water channels 3w and 5w to communicate with each other depending on an advanced or retracted position of the air/water valve.

The suction cylinder 4s includes a cylinder opening 4p. The suction tubes 3s and 5s are connected to the suction cylinder 4s, to enable the suction tubes 3s and 5s to communicate with each other depending on an advanced or retracted position of the suction valve.

Note that in the endoscope 1, a bending portion (not illustrated) is provided in the distal end portion of the insertion section 5, and the operation section 4 is provided with a bending knob for a bending operation of the bending portion, a freeze button for shooting, and the like, which are neither illustrated nor described herein.

(Configuration of Endoscope Reprocessor 11)

The endoscope reprocessor 11 is an apparatus that performs reprocessing for the contaminated endoscope 1 and a component, an accessory, or the like of the endoscope 1. The reprocessing is not particularly limited, but may be rinsing with water, cleaning for removing a contaminant such as an organic contaminant, disinfection for neutralizing a predetermined microorganism, sterilization for eliminating or killing all microorganisms, or any one of their combinations. The accessory is not particularly limited, but an example of the accessory is an air/water feeding valve, and a suction valve, or a distal end cover covering the distal end portion of the endoscope 1, which is mounted on the endoscope 1 at the time of use and removed from the endoscope 1 at the time of reprocessing.

The endoscope reprocessor 11 includes a treatment basin 21, an electromagnetic valve 31, air compressors 41 and 42, and a control section 51.

The treatment basin 21 is formed in a concave shape such that a liquid such as a cleaning liquid or a disinfecting liquid or a rinsing liquid can be reserved and the endoscope 1 can be arranged. The treatment basin 21 is provided with connectors 22a, 22b, 22c, 22d, 22e, and 22f. The connectors 22a, 22b, 22c, 22d, 22e, and 22f are each referred to as a connector 22 when any one or all of them is/are referred to.

The connector 22 may be provided outside the treatment basin 21, although provided inside the treatment basin 21 in FIG. 1.

The connector 22a as a first connector receptacle is connected to a connector for air/water cylinder C1aw and a connector for suction cylinder C1s as a first connector C1 via a tube T.

The connector for air/water cylinder C1aw and the connector for suction cylinder C1s each include a member that expands by air supply from the connector 22a and contracts by gas discharge into the connector 22a.

The connector for air/water cylinder C1aw enters a sealed state, described below, by adhering to the cylinder opening 4o when it expands by air supply after being inserted into the air/water cylinder 4aw. On the other hand, the connector for air/water cylinder C1aw enters an unsealed state, described below, because the adhesion to the cylinder opening 4o is released when it contracts by gas discharge. However, a structure in which the cylinder is brought into a sealed state and an unsealed state is not limited to the above-described structure but can be appropriately designed.

The connector for suction cylinder C1s enters a sealed state by adhering to the cylinder opening 4p when it expands by air supply after being inserted into the suction cylinder 4s. On the other hand, the connector for suction cylinder C1s enters an unsealed state because the adhesion to the cylinder opening 4p is released when it contracts by gas discharge.

The sealed state means a state where gas in the cylinders does not leak out of the endoscope 1 from between the first connector C1 and the cylinders. In the sealed state, the air channels 3a and 5a enter a communication state, and the water channels 3w and 5w are respectively separated from the air channels 3a and 5a by a separate section 4d to enter a communication state. On the other hand, the unsealed state means a state where gas in the cylinders leaks out of the endoscope 1 from between the first connector C1 and the cylinders. Note that the air/water cylinder 4aw need not include the separate section 4d.

That is, the first connector receptacle connects the first connector C1 connected to the cylinders provided in the operation section 4 in the endoscope 1 and switchable to a sealed state where gas does not leak out of the endoscope 1 from the cylinders and an unsealed state where gas leaks out of the endoscope 1 from the cylinders.

The connector 22b as a second connector receptacle is connected to second connectors C2a, C2b, C2c, C2d, and C2e via a tube T. The second connectors C2a, C2b, C2c, C2d, and C2e are each referred to as a second connector C2 when any one or all of them is/are referred to.

The second connector C2 is attached to the air supply connectors 2a and 2b, the water supply connector 2c, the suction connector 2d, and the instrument channel port 2e. The air supply connectors 2a and 2b, the water supply connector 2c, the suction pipe sleeve 2d, and the instrument channel port 2e are each referred to as a gas introduction port M when any one or all of them is/are referred to.

That is, the second connector receptacle connects a second connector C2 capable of switching the gas introduction port M to one of a sealed state and an unsealed state.

The sealed state means a state where gas does not leak out of the endoscope 1 from between the second connector C2 and the gas introduction port M. The unsealed state means a state where gas leaks out of the endoscope 1 from between the second connector C2 and the gas introduction port M.

For example, the second connector C2 is formed in a headed cylindrical shape to be externally fittable in the gas introduction port M, and includes a packing member, which expands by air supply from the connector 22b and contracts by gas discharge into the connector 22b, on the inner periphery side. The second connector C2 enters a sealed state when the packing member expands by air supply. On the other hand, the second connector C2 enters an unsealed state when the packing member contracts by gas discharge. However, a structure in which the gas introduction port is brought into a sealed state and an unsealed state is not limited to the above-described structure but can be appropriately designed.

The connector 22c is connected to the second connector C2e via a tube T. The second connector C2e is attached to the instrument channel port 2e. The instrument channel port 2e communicates with the instrument channel 5t.

The connector 22d is connected to the second connectors C2b and C2c via a tube T. The second connectors C2b and C2c are respectively attached to the air supply connector 2b and the water supply connector 2c. The air supply connector 2b and the water supply connector 2c respectively communicate with the air channel 3a and the water channel 3w.

The connector 22e is connected to the second connector C2a via a tube T. The second connector C2a is attached to the air supply connector 2a. The air supply connector 2a communicates with the air channel 3a.

The connector 22f is connected to the suction pipe sleeve 2d and connected to the suction tube 3s via a tube T and the second connector C2d.

Electromagnetic valves 31a, 31b, 31c, 31d, 31e, and 31f are connected to the connector 22. The electromagnetic valves 31a, 31b, 31c, 31d, 31e, and 31f are each hereinafter referred to as an electromagnetic valve 31 when any one or all of them is/are referred to.

The electromagnetic valve 31 is also connected to the control section 51, performs a valve opening/closing operation under the control of the control section 51, and supplies gas supplied from the air compressors 41 and 42 to the connector 22.

The air compressor 41 is connected to the electromagnetic valves 31a and 31b and the control section 51, and supplies gas to the connectors 22a and 22b, respectively, via the electromagnetic valves 31a and 31b under the control of the control section 51. An air release valve 41a is interposed between the air compressor 41 and the electromagnetic valves 31a and 31b. The air release valve 41a is connected to the control section 51, and discharges gas within the first connector C1 and the second connector C2 under the control of the control section 51.

The air compressor 42 is connected to the electromagnetic valves 31c, 31d, 31e, and 31f and the control section 51, and supplies gas to the connectors 22c, 22d, 22e, and 22f, respectively, via the electromagnetic valves 31c, 31d, 31e, and 31f under the control of the control section 51.

That is, a first switching device includes the connector 22a, the electromagnetic valve 31a, the air compressor 41, and the air release valve 41a. The first switching device switches the first connector C1 to one of a sealed state and an unsealed state.

A second switching device includes the connector 22b, the electromagnetic valve 31b, the air compressor 41, and the air release valve 41a. The second switching device switches the second connector C2 to one of a sealed state and an unsealed state.

A first gas feeding device includes the connectors 22d, 22e, and 22f, the electromagnetic valves 31d, 31e, and 31f, and the air compressor 42. The first gas feeding device introduces gas into the gas introduction port M. A first gas feeding device for water channel includes the connector 22d, the electromagnetic valve 31d, and the air compressor 42. A first gas feeding device for air channel includes the connectors 22d and 22e, the electromagnetic valves 31d and 31e, and the air compressor 42. A first gas feeding device for suction channel includes the connector 22f, the electromagnetic valve 31f, and the air compressor 42.

That is, the first gas feeding device is connected to the gas introduction port M provided in the scope connector 2 in the endoscope 1 to introduce gas and feed gas to a distal end of the endoscope 1 via the cylinder. The first gas feeding device is at least one of the first gas feeding device for air channel connected to the air channel 3a in the endoscope 1 and the first gas feeding device for water channel connected to the water channel 3w in the endoscope 1. The first gas feeding device is the first gas feeding device for suction channel connected to the suction channel 3s in the endoscope 1.

A second gas feeding device includes the connector 22c, the electromagnetic valve 31c, and the air compressor 42. The second gas feeding device introduces gas into the instrument channel port 2e in the endoscope 1.

The control section 51 includes a CPU (central processing unit) 51a and a memory 51b. A function of the control section 51 is implemented when a program P stored in the memory 51b is read out and executed by the CPU 51a. The program P for endoscope dewatering treatment, for example, is stored in the memory 51b.

The control section 51 can control respective operations of the electromagnetic valve 31, the air compressors 41 and 42, and the air release valve 41a. The control section 51 outputs a control signal for causing the electromagnetic valve 31 and the air release valve 41a to each perform a valve opening/closing operation. The control section 51 outputs a control signal for driving and stopping the air compressors 41 and 42.

The control section 51 controls the first switching device and the first gas feeding device such that first driving for driving the first gas feeding device by bringing the first connector C1 into the unsealed state is performed and second driving for driving the first gas feeding device by bringing the first connector C1 into the sealed state is then performed, for example.

The control section 51 performs control such that the second gas feeding device is driven when the first driving and the second driving are performed, for example.

The control section 51 performs control to bring the connector for air/water cylinder C1aw inserted into the air/water cylinder 4aw in the endoscope 1 into an unsealed state to introduce gas from the air supply connectors 2a and 2b and the water supply connector 2c in the endoscope 1 and then bring the connector for air/water cylinder c1aw into a sealed state to introduce gas from the air supply connectors 2a and 2b and the water supply connector 2c in the endoscope 1, for example.

The control section 51 performs control to bring the connector for suction cylinder C1s inserted into the suction cylinder 4s in the endoscope 1 into an unsealed state to introduce gas from the suction pipe sleeve 2d in the endoscope 1 and then bring the connector for suction cylinder C1s into a sealed state to introduce gas from the suction pipe sleeve 2d in the endoscope 1, for example.

(Function)

An operation of endoscope dewatering treatment by the endoscope reprocessor 11 will be described.

Figure 2:
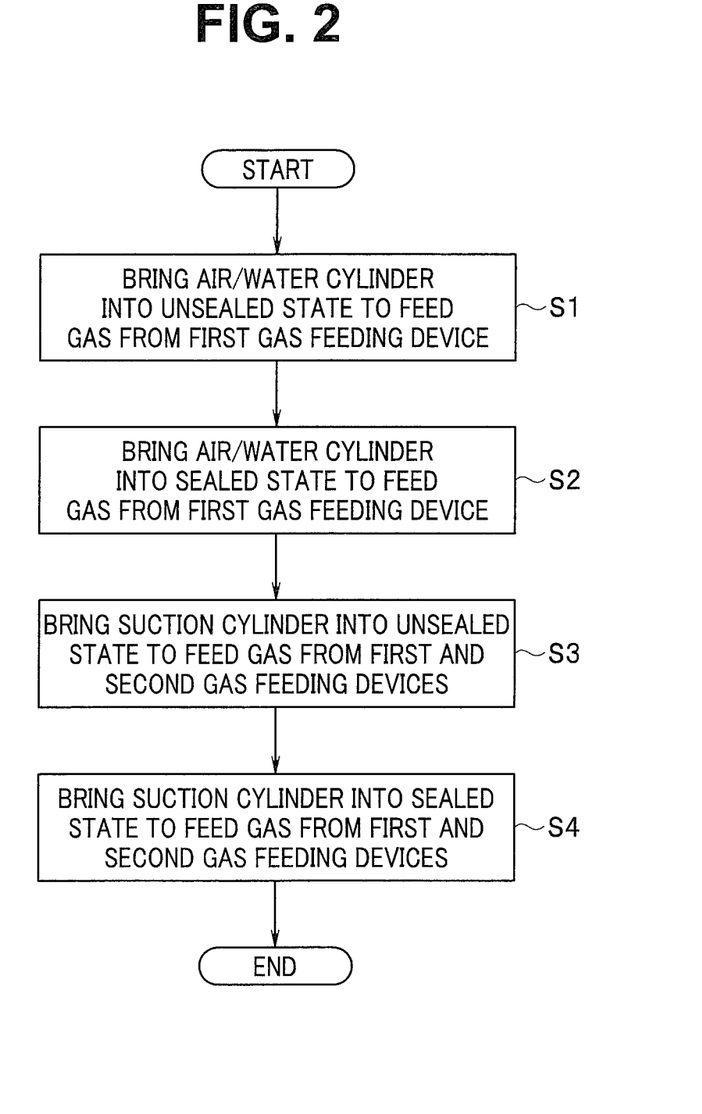
FIG. 2 is a flowchart illustrating an example of flow of endoscope dewatering treatment by the endoscope reprocessor according to the embodiment of the present invention.
Figure 3:
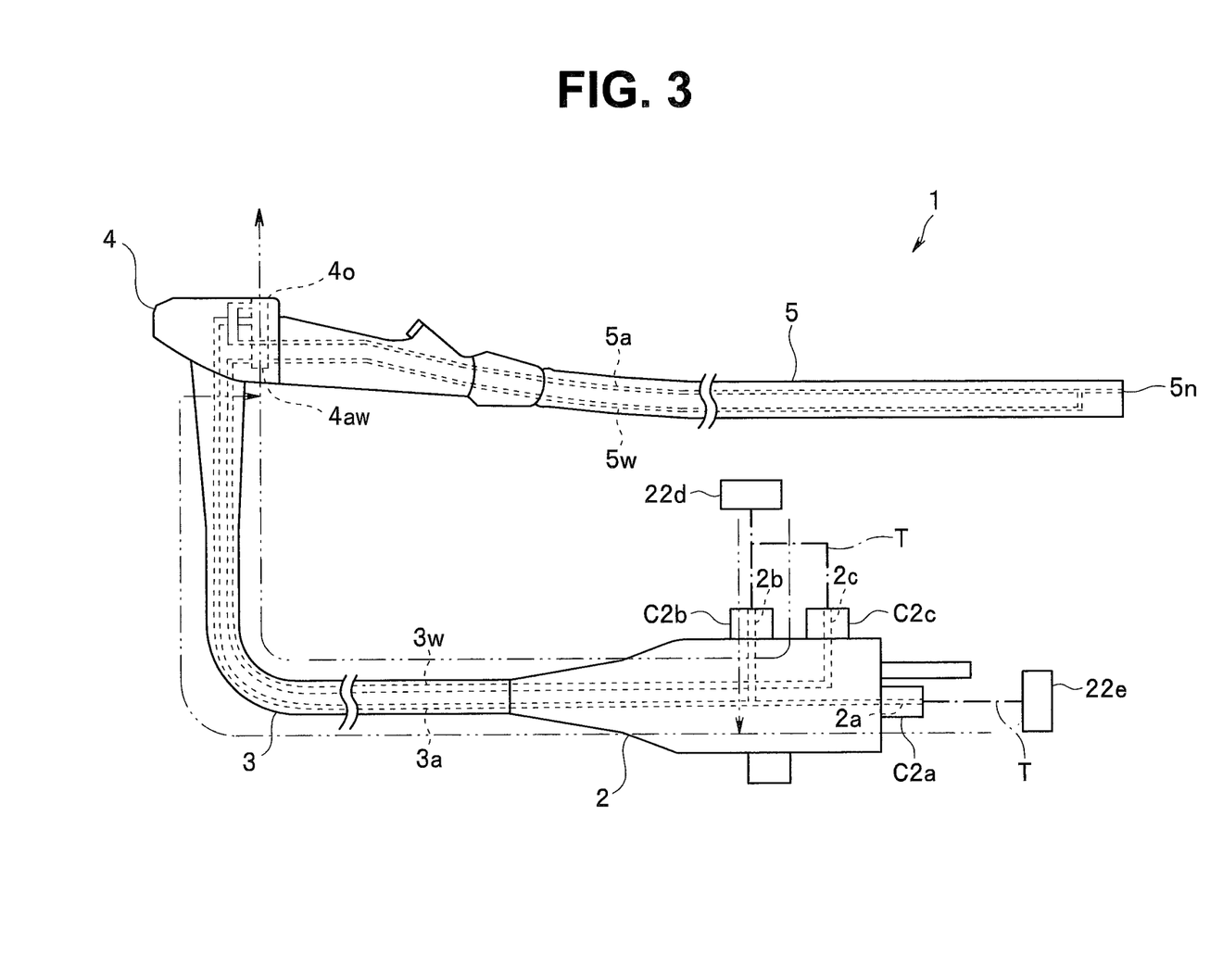
FIG. 3 is a diagram for describing flow of gas in an air channel and a water channel in an unsealed state of the endoscope reprocessor according to the embodiment of the present invention.

FIG. 2 is a flowchart illustrating an example of flow of endoscope dewatering treatment by the endoscope reprocessor 11 according to the embodiment of the present invention. FIG. 3 is a diagram for describing flow of gas in the air channel 3a and the water channel 3w in an unsealed state of the endoscope reprocessor 11 according to the embodiment of the present invention. In FIG. 3, the air/water cylinder 4aw is in an unsealed state, and the connector for air/water cylinder C1aw is omitted.

After reprocessing by introducing a liquid into a conduit of the endoscope, such as cleaning treatment, disinfecting treatment, or rinsing treatment is performed, and the liquid is discharged from the treatment basin 21, the CPU 51a executes the program P for endoscope dewatering treatment stored in the memory 51b.

The air/water cylinder 4aw is brought into an unsealed state to feed gas from the first gas feeding device (S1). The control section 51 outputs a control signal for bringing the electromagnetic valve 31a into an open state, to bring the electromagnetic valve 31a into the open state. The control section 51 outputs a control signal for bringing the air release valve 41a into an open state, to bring the air release valve 41a into the open state. As a result, the control section 51 discharges gas in the connector for air/water cylinder c1aw via the air release valve 41a, to bring the air/water cylinder 4aw into the unsealed state. Then, the control section 51 outputs a control signal for bringing the electromagnetic valves 31d and 31e into an open state, to bring the electromagnetic valves 31d and 31e into the open state. The control section 51 outputs a control signal for bringing the second connector C2 into a sealed state such that a total amount of gas fed from the first gas feeding device is introduced into the conduit of the endoscope 1, to bring the second connector C2 into the sealed state. The control section 51 outputs a driving signal for driving the air compressor 42 such that gas can be fed from the first gas feeding device, to drive the air compressor 42. Consequently, gas is introduced into the air supply connector 2b and the water supply connector 2c from the connector 22d, and gas is introduced into the air supply connector 2a from the connector 22e. Gas introduced from the air supply connectors 2a and 2b pushes residual fluid in the air channel 3a and the air/water cylinder 4aw, and discharges the residual fluid outward from the endoscope 1 through the air/water cylinder 4aw. Gas introduced from the water supply connector 2c pushes residual fluid in the water channel 3w and the air/water cylinder 4aw, and discharges the residual fluid outward from the endoscope 1 through the air/water cylinder 4aw.

Figure 4:
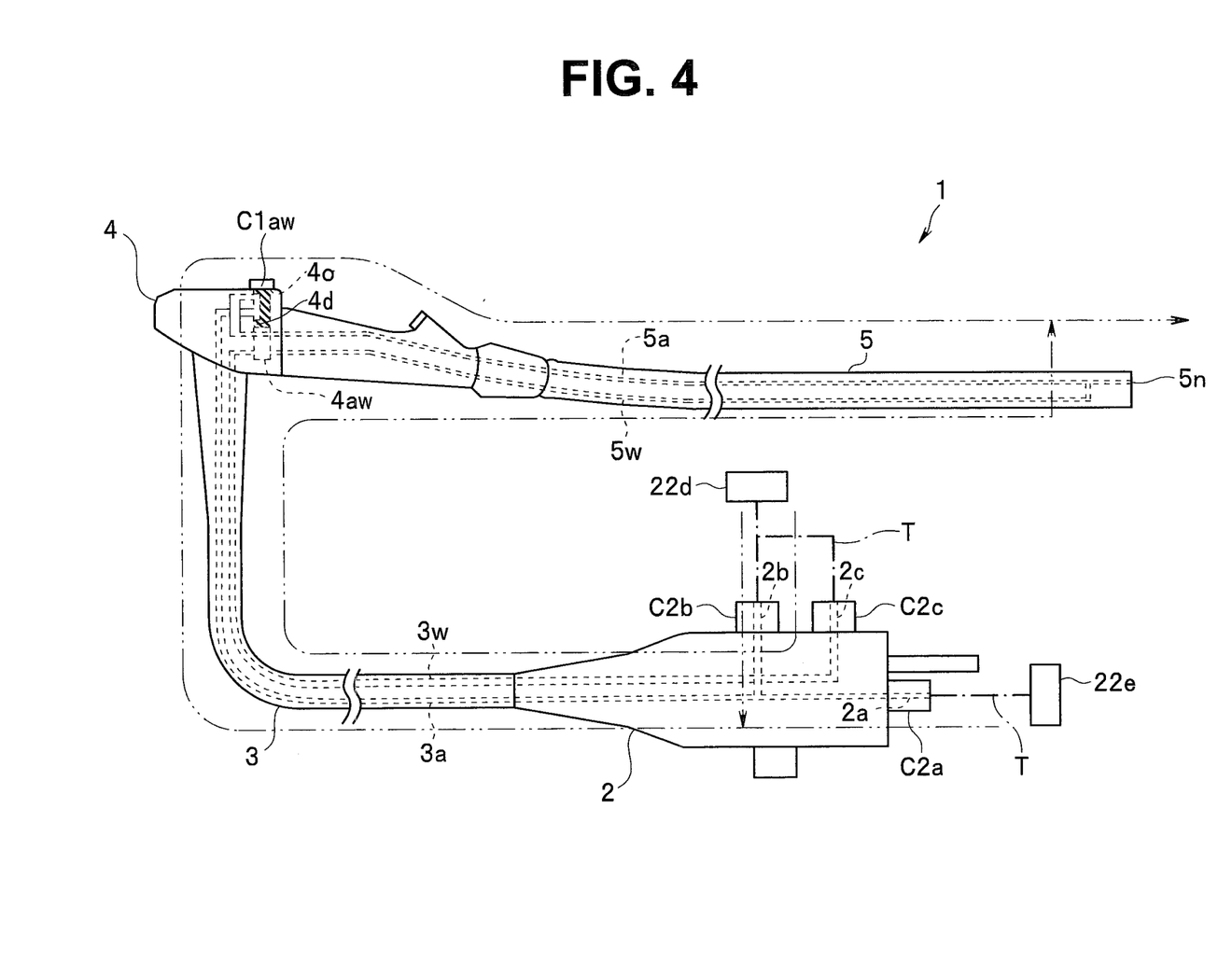
FIG. 4 is a diagram for describing flow of gas in the air channel and the water channel in a sealed state of the endoscope reprocessor according to the embodiment of the present invention.

FIG. 4 is a diagram for describing flow of gas in the air channels 3a and 5a and the water channels 3w and 5w in a sealed state of the endoscope reprocessor 11 according to the embodiment of the present invention.

The air/water cylinder 4aw is brought into a sealed state to feed gas from the first gas feeding device (S2). The control section 51 outputs a control signal, to bring the air release valve 41a into a sealed state, drives the air compressor 41, and supplies gas to the connector for air/water cylinder C1aw from the connector 22a, to bring the air/water cylinder 4aw into the sealed state. When the air/water cylinder 4aw is brought into the sealed state, gas introduced into the air supply connectors 2a and 2b by the first gas feeding device pushes residual fluid in the air channel 5a, and discharges the residual fluid outward from the endoscope 1 through the air/water feeding nozzle 5n. Gas introduced into the water supply connector 2c pushes residual fluid in the water channel 5w, and discharges the residual fluid outward from the endoscope 1 through the air/water feeding nozzle 5n.

Figure 5:
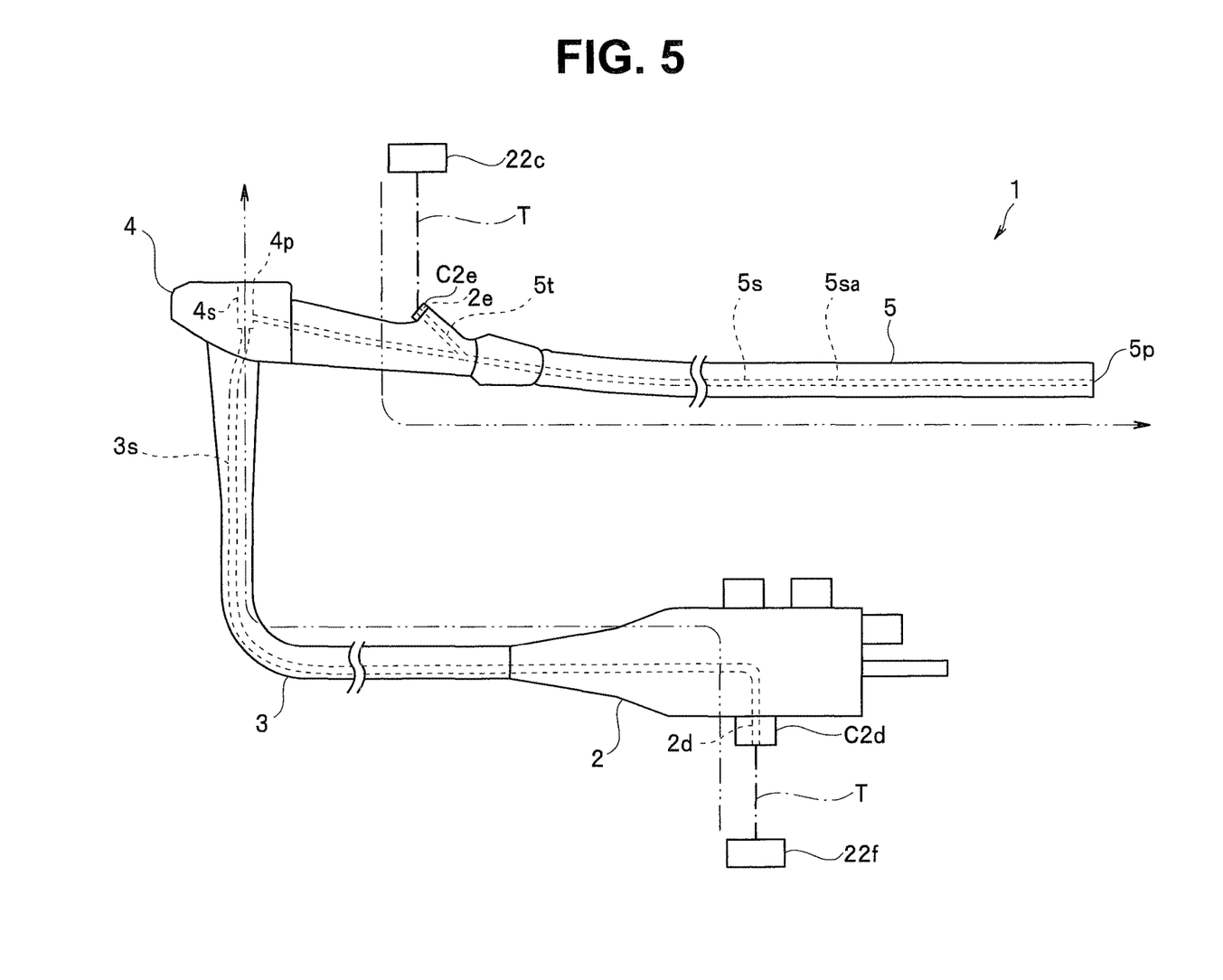
FIG. 5 is a diagram for describing flow of gas in a suction channel and an instrument channel in the unsealed state of the endoscope reprocessor according to the embodiment of the present invention.

FIG. 5 is a diagram for describing flow of gas in the suction tubes 3s and 5s and the instrument channel 5t in an unsealed state of the endoscope reprocessor 11 according to the embodiment of the present invention. In FIG. 5, the suction cylinder 4s is in an unsealed state, and the connector for suction cylinder C1s is omitted.

The suction cylinder 4s is brought into an unsealed state to feed gas from the first and second gas feeding devices (S3). The control section 51 outputs a control signal, to bring the electromagnetic valve 31a into an open state and bring the air release valve 41a into an open state, and discharges gas in the connector for suction cylinder C1s, to bring the suction cylinder 4s into the unsealed state. Then, the control section 51 outputs a control signal, and drives the first gas feeding device to introduce gas into the suction tube 3s from the connector 22f via the suction pipe sleeve 2d while driving the second gas feeding device to introduce gas into the instrument channel 5t from the connector 22c via the instrument channel port 2e. Gas introduced into the suction pipe sleeve 2d pushes residual fluid in the suction tube 3s and the suction cylinder 4s, and discharges the residual fluid outward from the endoscope 1 through the suction cylinder 4s brought into the unsealed state. Gas introduced from the instrument channel port 2e pushes residual fluid in the instrument channel 5t and a suction tube 5sa closer to a distal end than a branch portion of the instrument channel 5t, and discharges the residual fluid outward from the endoscope 1 through the distal end opening 5p.

Figure 6:
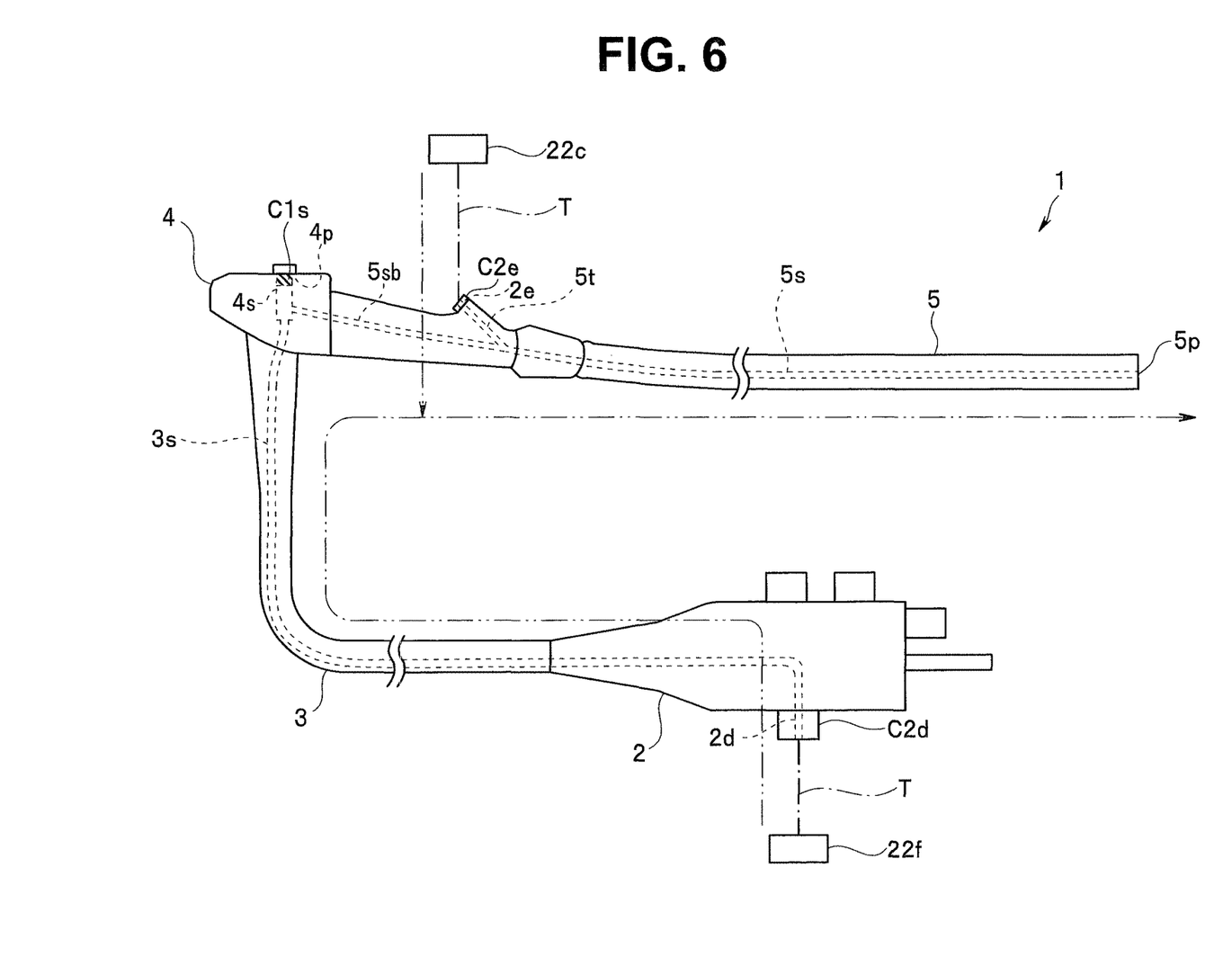
FIG. 6 is a diagram for describing flow of gas in the suction channel and the instrument channel in the sealed state of the endoscope reprocessor according to the embodiment of the present invention.

FIG. 6 is a diagram for describing flow of gas in the suction tubes 3s and 5s and the instrument channel 5t in a sealed state of the endoscope reprocessor 11 according to the embodiment of the present invention.

The suction cylinder 4s is brought into a sealed state to feed gas from the first and second gas feeding devices (S4). The control section 51 outputs a control signal, to bring the air release valve 41a into a closed state, drives the air compressor 41, and supplies gas to the connector for suction cylinder C1s from the connector 22a, to bring the suction cylinder 4s into the sealed state. The control section 51 drives the first gas feeding device to introduce gas into the suction tube 3s from the connector 22f via the suction pipe sleeve 2d while driving the second gas feeding device to introduce gas into the instrument channel 5t from the connector 22c via the instrument channel port 2e. Gas introduced into the suction pipe sleeve 2d is introduced into the suction tube 5s via the suction cylinder 4s, to push residual fluid in a suction tube 5sb from the suction cylinder 4s to the branch portion of the instrument channel 5t and discharge the residual fluid outward from the endoscope 1 through the distal end opening 5p.

Processes in steps S1 to S4 constitute the endoscope dewatering treatment.

As a result, the endoscope reprocessor 11 can reliably remove water in the endoscope 1 from the scope connector 2 to the distal end of the insertion section 5 by feeding gas into the scope connector 2. In the endoscope reprocessor 11, a distance for which residual fluid in the endoscope 1 is pushed is shortened. Accordingly, conduit resistance by gas feeding is low, and a time period required for dewatering is also shortened.

According to the above-described embodiment, the endoscope reprocessor 11 can shorten a time period required to remove water in the endoscope 1.

Note that, although the first connector C1 includes the connector for air/water cylinder C1aw and the connector for suction cylinder C1s in the embodiment, the first connector C1 may be one connector insertable into both the air/water cylinder 4aw and the suction cylinder 4s. The connector for air/water cylinder C1aw and the connector for suction cylinder C1s may be integrally formed.

Note that, although the first connector C1 and the second connector C2 are each switched between the sealed state and the unsealed state by supplying gas in the embodiment, the present invention is not limited to this. For example, the sealed state and the unsealed state may be switched by supplying a liquid, may be switched by pressing a seal member under fluid pressure and a restoring force of a spring, may be switched by sliding the seal member by motor driving, or may be switched by pulling a wire attached to the seal member by motor driving.

Although gas is fed from the first gas feeding device and the second gas feeding device by bringing the second connector C2 into the sealed state in the embodiment, gas may be fed from the first gas feeding device and the second gas feeding device by bringing the second connector C2 into the unsealed state.

Each "section" in the present specification is not necessarily in a one-to-one correspondence with specific hardware or a software routine. Therefore, in the present specification, the embodiment has been described, assuming a virtual circuit block (section) having each of functions in the embodiment. A plurality of steps in each procedure in the present embodiment may be executed by changing an execution order, may be executed simultaneously, or may be executed in an order which differs for each execution as long as each of the steps is not contrary to its property. Further, all or some of the steps in each procedure in the present embodiment may be implemented by hardware.

The present invention is not limited to the above-described embodiment, and various changes, alterations, and the like are possible without departing from the scope or spirit of the present invention.

According to the present invention, there can be provided an endoscope reprocessor and an endoscope dewatering method that enable a time period required to remove water in an endoscope to be shortened.

What is claimed is:

1. An endoscope reprocessor comprising:
a first connector receptacle configured to connect a first connector connected to a cylinder provided in an operation section in an endoscope and switchable to one of a sealed state where gas does not leak out of the endoscope from the cylinder and an unsealed state where gas leaks out of the endoscope from the cylinder;
a first switching device configured to switch the first connector to one of the sealed state and the unsealed state;
a first gas feeding device configured to introduce gas by being connected to a gas introduction port provided in a scope connector in the endoscope and feed gas to a distal end of the endoscope via the cylinder; and
a processor configured to control the first switching device and the first gas feeding device such that first driving for driving the first gas feeding device by bringing the first connector into the unsealed state is performed and second driving for driving the first gas feeding device by bringing the first connector into the sealed state is then performed.

2. The endoscope reprocessor according to claim 1, further comprising
a second connector receptacle configured to connect a second connector switchable to one of a sealed state where gas does not leak out of the endoscope from the gas introduction port and an unsealed state where gas leaks out of the endoscope, and
a second switching device configured to switch the second connector to one of the sealed state and the unsealed state,
wherein the first gas feeding device is connected to the gas introduction port via the second connector.

3. The endoscope reprocessor according to claim 1, wherein
the first connector receptacle is connected to a connector for air/water cylinder connected to an air/water cylinder in the endoscope, and
the first gas feeding device is at least one of a first gas feeding device for air feeding channel connected to an air feeding channel in the endoscope and a first gas feeding device for water feeding channel connected to a water feeding channel in the endoscope.

4. The endoscope reprocessor according to claim 1, wherein
the first connector receptacle is connected to a connector for suction cylinder connected to a suction cylinder in the endoscope, and
the first gas feeding device is a first gas feeding device for suction channel connected to a suction channel in the endoscope.

5. The endoscope reprocessor according to claim 4, further comprising
a second gas feeding device configured to introduce gas by being connected to an instrument channel port in the endoscope,
wherein the processor performs control such that the second gas feeding device is driven at the time of the first driving and the second driving.

6. An endoscope dewatering method comprising bringing a connector for air/water cylinder inserted into an air/water cylinder in an endoscope into an unsealed state where gas leaks out of the endoscope from the air/water cylinder to introduce gas from an air supply connector and a water supply connector in the endoscope, and then bringing the connector for air/water cylinder into a sealed state where gas does not leak out of the endoscope from the air/water cylinder to introduce gas from the air supply connector and the water supply connector in the endoscope.

7. An endoscope dewatering method comprising bringing a connector for suction cylinder inserted into a suction cylinder in an endoscope into an unsealed state where gas leaks out of the endoscope from the suction cylinder at the same time of introducing gas from a suction connector in the endoscope, and then bringing the connector for suction cylinder into a sealed state where gas does not leak out of the endoscope from the suction cylinder at the same time of introducing gas from a suction connector in the endoscope.

* * * * *